(12) United States Patent
Kusuzawa

(10) Patent No.: US 6,690,520 B1
(45) Date of Patent: *Feb. 10, 2004

(54) OPTICAL SYSTEM FOR VISUALIZING AN OBJECT IN A LIGHT SCATTERING MEDIUM

(75) Inventor: Hideo Kusuzawa, Kobe (JP)

(73) Assignee: Sysmex Corporation, Hyogo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/856,320

(22) Filed: May 14, 1997

(30) Foreign Application Priority Data

May 15, 1996 (JP) .............................................. 8-146576

(51) Int. Cl.[7] ............................ G02B 9/08; G01N 21/00
(52) U.S. Cl. ....................... 359/740; 359/368; 359/738; 356/343
(58) Field of Search ............................... 359/362–363, 359/368–372, 385–388, 738–740; 351/205–214; 356/336–343

(56) References Cited

U.S. PATENT DOCUMENTS

| | | | | |
|---|---|---|---|---|
| 2,977,847 A | * | 4/1961 | Meyer-Arendt | ............. 359/370 |
| 4,072,421 A | * | 2/1978 | Coyne et al. | ............. 356/338 |
| 4,927,267 A | * | 5/1990 | Herve | ............. 356/336 |
| 5,028,135 A | * | 7/1991 | Cheung | ............. 356/340 |
| 5,107,351 A | * | 4/1992 | Leib et al. | ............. 359/11 |
| 5,162,641 A | * | 11/1992 | Fountain | |
| 5,203,339 A | * | 4/1993 | Knuttel et al. | |
| 5,214,454 A | * | 5/1993 | Sano | ............. 351/206 |
| 5,410,156 A | * | 4/1995 | Miller | |
| 5,471,261 A | * | 11/1995 | Yoshizo et al. | ............. 351/214 |
| 5,493,121 A | * | 2/1996 | Fitzpatrick | |
| 5,764,358 A | * | 6/1998 | Heffels | ............. 356/343 |

OTHER PUBLICATIONS

"Microscope Imaging Through Highly Scattering Media"; G.E. Anderson, et al; Optics Letters, vol. 19, No. 13, Jul. 1, 1994.

* cited by examiner

Primary Examiner—Thong Nguyen
(74) Attorney, Agent, or Firm—Birch, Stewart, Kolasch & Birch, LLP

(57) ABSTRACT

An optical system for visualizing an object includes an object lens, an imaging lens disposed on an optical axis of the object lens, and a spatial filter disposed on the optical axis between the object lens and the imaging lens. The spatial filter includes a first portion away from the optical axis and a second portion adjacent to the optical axis, the first porting having a higher light transmittance than the second portion. The distance of the first portion from the optical axis is set to maximize the light from the object. This optical system is particularly useful for detecting an object in a light scattering medium. Movement of the optical system also allows a tomographic image to be generated.

19 Claims, 5 Drawing Sheets

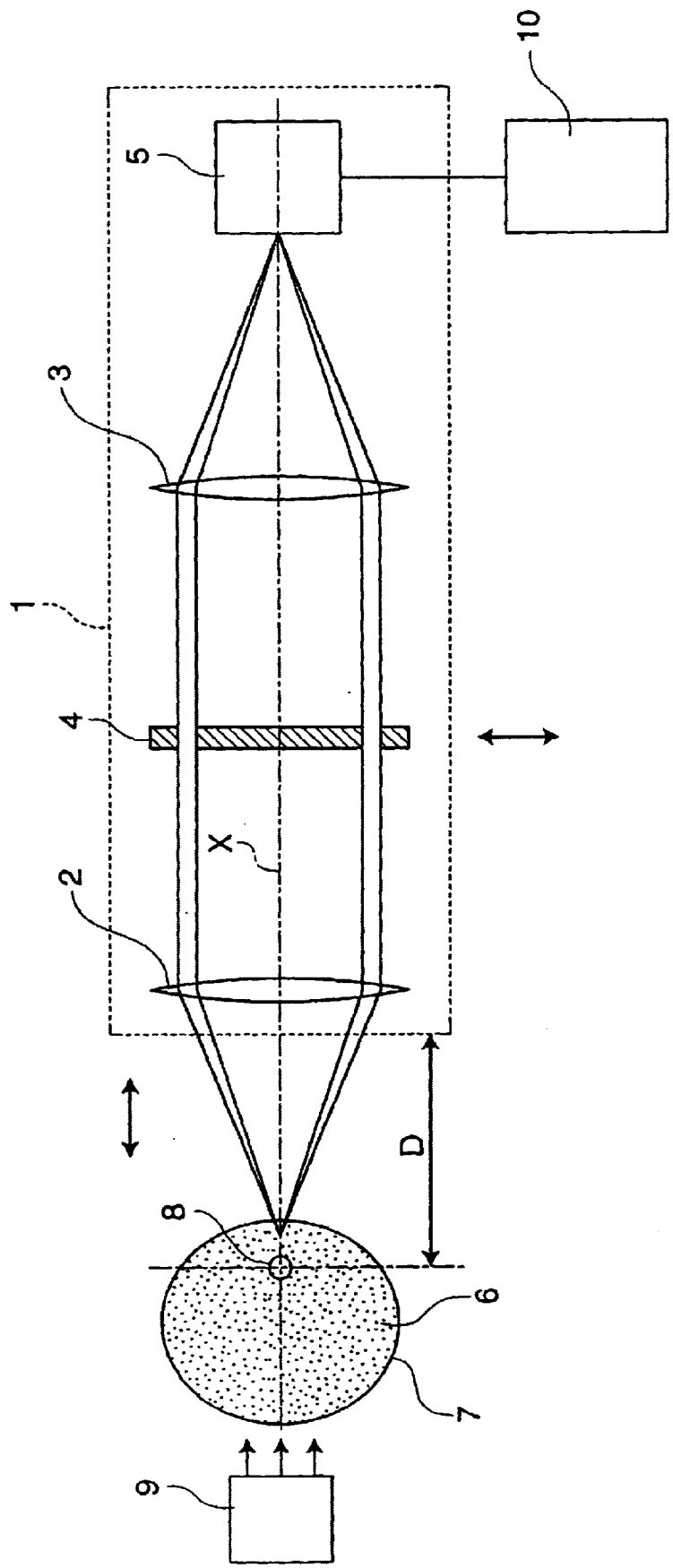

OPTICAL SYSTEM FOR VISUALIZING AN OBJECT IN A LIGHT SCATTERING MEDIUM

BACKGROUND OF THE INVENTION

1. Field of the Invention

The present invention relates to an optical system for visualizing an object in a light scattering medium. More particularly, the present invention relates to an optical system for visualizing and capturing a blood vessel in a tissue of a living body. The term "light scattering medium" as used herein includes also a light scattering and absorbing medium.

2. Description of the Related Arts

So far, there have been various attempts to visualize or image an object in a light scattering or absorbing medium (see, for example, "Microscope Imaging Through Highly Scattering Media", G. E. Anderson et al., OPTICS LETTERS, Vol. 19, No. 13 published on Jul. 1, 1994).

However, the conventional optical system utilizes a method of suppressing the influence of scattering by increasing the depth of focus in the optical system, so that the resolution is liable to decrease.

SUMMARY OF THE INVENTION

The present invention has been made in view of these circumstances and the purpose thereof is to provide an optical system capable of visualizing an object in a light scattering medium, without decreasing the resolution, by imaging with only a light beam emanated at a specific angle from the object in the light scattering medium.

The present invention provides an optical system for visualizing an object comprising an object lens, an imaging lens disposed on an optical axis of the object lens, and a spatial filter disposed on the optical axis between the object lens and the imaging lens, the spatial filter including a first portion away from the optical axis and a second portion adjacent to the optical axis, the first portion being higher than the second portion in light transmittance.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is an explanatory view of a construction of an embodiment according to the present invention.

DETAILED DESCRIPTION OF THE PREFERRED EMBODIMENTS

Figure 2A:
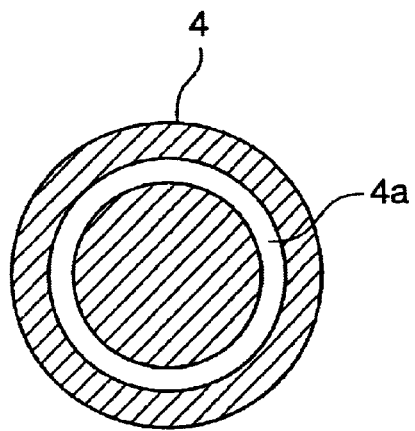
FIG. 2A is a front view of a mechanical configuration of the spatial filter of the embodiment according to the present invention.

When an object in a light scattering medium is viewed via optical system in accordance with the present invention, only a light beam of a specific angle among the light beams incident into the object lens from the object is mainly transmitted through the first portion of the spatial filter having a higher transmittance to be imaged by the imaging lens. Therefore, a visualization of the object can be improved since the scattered light beam incident at a different angle into the object lens from the light scattering medium is removed.

The present invention allows an object in a light scattering medium to be visualized. Here, the object in a light scattering medium may be, for example, a blood vessel in a tissue of a living body including a human body. In the present invention, the image formed by the imaging lens can be captured by an image capturing element such as a CCD.

Also, the object lens and the imaging lens are preferably arranged so that a rear focus of the object lens coincides with a front focus of the imaging lens, and the spatial filter is preferably disposed at the rear focus of the object lens. The object lens and the imaging lens each may be a commercially available lens such as an achromatic lens (diameter: 30 mm, focal length: 30 mm).

The spatial filter may be such that the first portion away from the optical axis is transparent and the second portion adjacent to the optical axis is opaque. Preferably, the spatial filter comprises a light blocking plate having an annular slit with, for example, a radius of 5 to 13 mm and a width of 1 to 3 mm for transmitting a light. Preferably, the spatial filter is exchangeable. This allows the radius and the width of the annular slit to be adjusted in accordance with the scattering properties of the light scattering medium and the object. In this instance, the radius and the width of the annular slit are preferably adjusted so that the annular slit transmits the light which maximizes the difference in intensity distribution between the scattered light from the medium and the diffracted light from the periphery of the object.

More preferably, the spatial filter comprises a light transmitting liquid crystal panel capable of locally changing the light transmittance by means of an electric signal because it facilitates the formation of the annular slit and the adjustment of its radius and width.

EXAMPLES

FIG. 1 is an explanatory view of a construction of an embodiment according to the present invention. Referring to FIG. 1, an optical system 1 comprises an object lens 2, an imaging lens 3 disposed on the optical axis X of the object lens 2, and a spatial filter 4 disposed between the object lens 2 and the imaging lens 3. An image capturing element (CCD) 5 is arranged so as to capture an image formed by the imaging lens 3. The captured image is displayed on a CRT of a monitor television 10. Here, the object lens 2 and the imaging lens 3 each have a diameter of 30 mm and a focal length of 30 mm.

Referring to FIG. 2A, the spatial filter 4 includes an annular, light transmitting slit 4a so that a portion (a first portion) away in a radial direction from the optical axis has a higher light transmittance than the other portion (a second portion) which is formed to block light. The spatial filter 4 may be obtained, for example, by laminating a light-blocking film on portions of a transparent resin film or a transparent glass plate other than the annular slit 4a.

The annular slit 4a has a radius of 9 mm and a width of 2 mm.

Figure 2B:
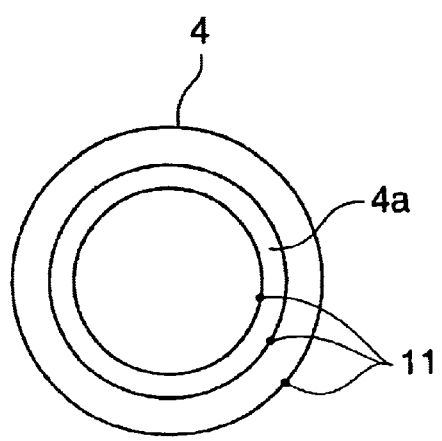
FIG. 2B is a front view of an electrical configuration of the spatial filter of the present invention.

Alternatively, as shown in FIG. 2B, the spatial filter 4 is a light transmitting liquid crystal display panel capable of locally changing the light transmittance in accordance with electric signals supplied by leads 11. As in FIG. 2B the annular slit 4a is controlled to have a light transmittance which is larger than a portion of the spatial filter which is adjacent to the optical axis.

The object lens 2 and the imaging lens 3 are arranged so that their focal lengths/lens diameters are the same with each other and the rear focus of the object lens 2 coincides with the front focus of the imaging lens 3, whereby the two lenses 2, 3 are in conjugate relation. The spatial filter 4 is disposed at the rear focus of the object lens 2, namely, at the front focus of the imaging lens 3.

Figure 3:
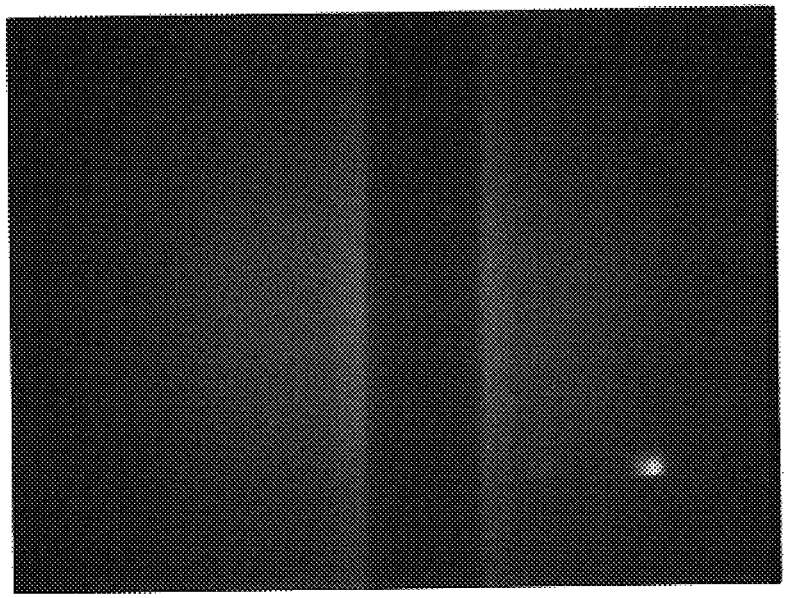
FIG. 3 is a photograph showing a half-tone image display on a CRT in the embodiment according to the present invention.

As shown in FIG. 1, an object 8 (here, a capillary having an outer diameter of 1.2 mm and an inner diameter of 1.0 mm and containing a blood) is inserted into a tubular transparent glass vessel 7 having an outer diameter of 22 mm and an inner diameter of 20 mm and containing a light scattering medium 6 (here, a commercially available milk). The vessel 7 is illuminated from a rear surface by a light source 9, and an image of the object 8 is captured by the optical system 1. An example of the image obtained by this operation is shown in FIG. 3.

Figure 4:
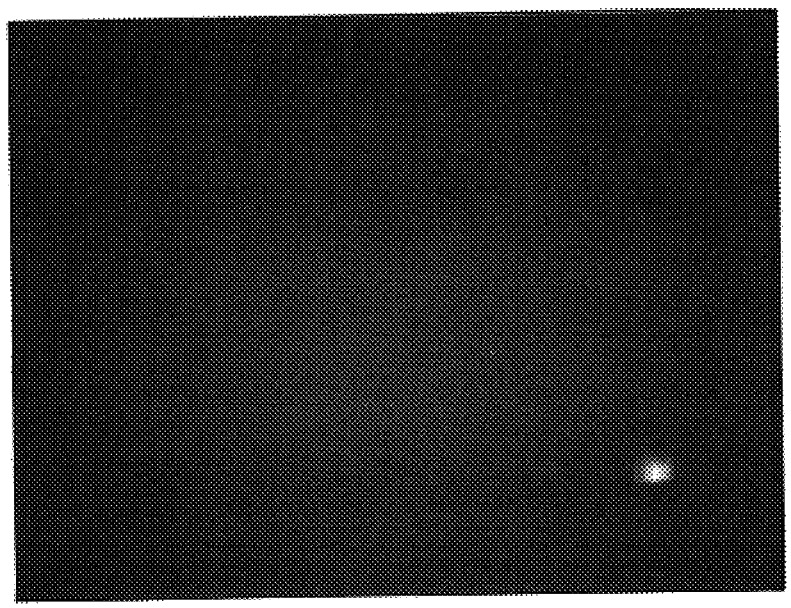
FIG. 4 is a photograph showing a half-tone image displayed on a CRT in a comparative example.

An example of the image obtained by means of an image capturing device having an ordinary television lens instead of the optical system 1 is shown in FIG. 4 as a comparative example. Comparing FIGS. 3 and 4, it will be understood that the image of the object (the capillary) 8 totally unobservable in FIG. 4 is clearly captured in FIG. 3.

In other words, when a transmitting illumination (a backlight illumination) from the light source 9 is conducted onto the object 8 in the light scattering medium 6, as shown in FIG. 1, scattering and diffraction take place at the interface between the object 8 and the medium 6, and the light absorbed/scattered in the object 8 is transmitted. The optical system 1 then restricts this transmitted light with the spatial filter 4 to allow only the light beam incident at a specific angle to pass and be imaged, whereby the image of the object 8 in the light scattering medium 6 is clearly captured as shown in FIG. 3. This effect is brought about by the fact that the S/N ratio increases because of reduced disturbing scattering light intensity from the light scattering medium 6 by using the spatial filter 4.

Figure 5:
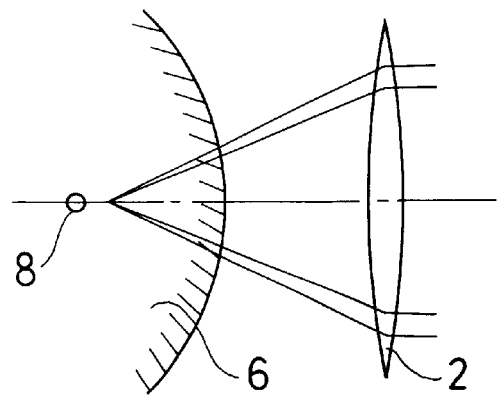
FIG. 5 is an explanatory view for capturing a tomography image (sectional photograph) with the optical system focused in front of the object in the embodiment according to the present invention.
Figure 6:
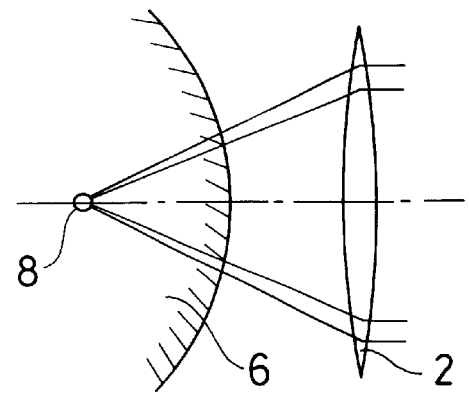
FIG. 6 is an explanatory view for capturing a tomography image (sectional photograph) with the optical system focussed at the object in the embodiment according to the present invention.
Figure 7:
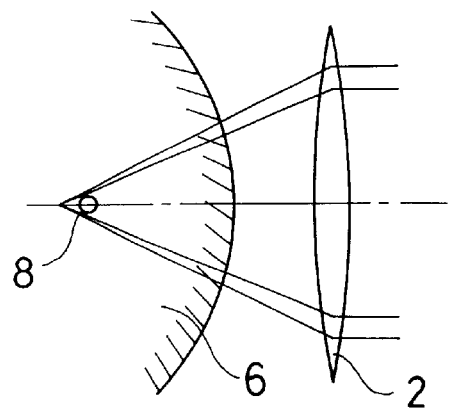
FIG. 7 is an explanatory view for capturing a tomography image (sectional photograph) with the optical system focussed behind the object in the embodiment according to the present invention.

Further, referring to FIGS. 5 to 7, the position of the focus of the object lens 2 relative to the object 8 changes when the distance D between the optical system 1 and the object 8 is varied by moving the optical system 1 in the direction of the optical axis X. This allows a tomography image (sectional photograph) to be captured with respect to the direction of the optical axis (the direction of depth).

Figure 8:
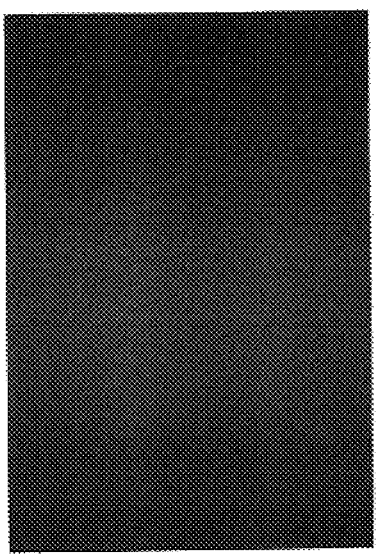
FIG. 8 is a photograph showing a half-tone image displayed on a CRT in the embodiment according to the present invention at the focus shown in FIG. 5.
Figure 9:
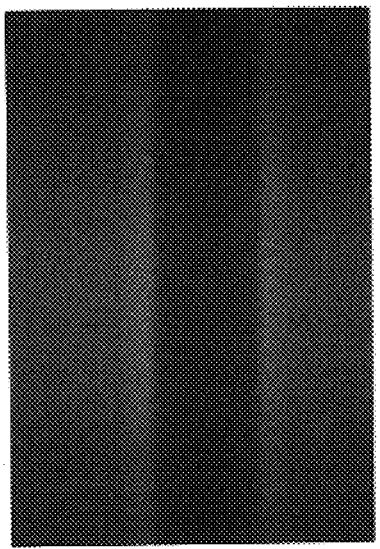
FIG. 9 is a photograph showing a half-tone image displayed on a CRT in the embodiment according to the present invention at the focus shown in FIG. 6.
Figure 10:
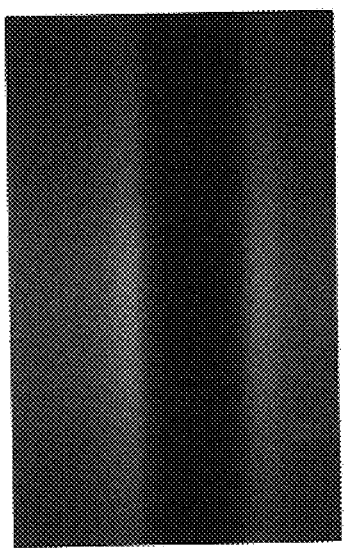
FIG. 10 is a photograph showing a half-tone image displayed on a CRT in the embodiment according to the present invention at the focus shown in FIG. 7.

Examples of the captured images obtained corresponding to FIGS. in which the focus of the optical system is in front of, on and behind the object, respectively 5 to 7 are shown in FIGS. 8 to 10, respectively. Also, the position of the object 8 relative to the vessel 7 can be accurately detected by finding the distance D at which the sharpest image (here, FIG. 9) is obtained in capturing the tomography images.

According to the present invention, an object in a light scattering medium can be clearly visualized because imaging is performed by using only a light beam incident at a specific angle.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim is:

1. An optical system for obtaining a tomography image of an object in a light scattering medium comprising:
    an object lens;
    an imaging lens disposed on an optical axis of the object lens;
    a spatial filter disposed on the optical axis between the object lens and the imaging lens, the spatial filter including a first portion away from the optical axis and a second portion adjacent to the optical axis; and
    an image capturing element for capturing the tomography image of the object through the imaging lens by adjusting a focus position of the object lens relative to the object,
    wherein the first portion of the spatial filter transmits light which is incident on the object lens at a predetermined angle with respect to the optical axis so as to transmit light from the object, and the second portion of the spatial filter blocks light which is incident on the object lens at an angle smaller than the predetermined angle with respect to the optical axis so as to block light from the light scattering medium.

2. An optical system for visualizing an object according to claim 1, wherein the spatial filter comprises a light blocking plate having an annular slit for transmitting light.

3. An optical system for visualizing an object according to claim 2, wherein the annular slit has a radius of 5 to 13 mm and a width of 1 to 3 mm.

4. An optical system for visualizing an object according to claim 1, wherein the spatial filter is exchangeable.

5. An optical system for visualizing an object according to claim 1, wherein the spatial filter comprises a light transmitting liquid crystal panel capable of locally changing the light transmittance by means of an electric signal.

6. An optical system for visualizing an object according to claim 5, wherein the liquid crystal panel forms an annular slit whose radius and width can be adjusted by means of the electric signal.

7. An optical system for visualizing an object according to claim 1, wherein said spatial filter blocks light from the light scattering medium and passes light from the object; and a distance of the first portion away from the optical axis and a size of the first portion is variable so that said spatial filter is capable of blocking light from the light scattering medium and passing light from the object under various conditions.

8. An optical system for visualizing an object according to claim 1, wherein the spatial filter further includes a third portion further away from the optical axis than the first portion, the first portion having a higher light transmittance than the third portion.

9. An optical system for visualizing an object according to claim 1, further comprising a light source for illuminating the object in the light scattering medium.

10. An optical system for visualizing an object according to claim 1, wherein the spatial filter reduces a distributed intensity of light from the scattering medium.

11. An optical system for visualizing an object according to claim 1, wherein the object lens collimates light from the object.

12. An optical system according to claim 1, wherein a depth of the object in the light scattering medium is detected by sharpness of the tomography image.

13. An optical system according to claim 1,
wherein the object in the light scattering medium is a blood vessel in a tissue of a living body.

14. An optical system for obtaining a tomography image of an object in a light scattering medium comprising:
a light source for illuminating the object in the light scattering medium;
an object lens;
an imaging lens disposed on an optical axis of the object lens;
a spatial filter disposed on the optical axis between the object lens and the imaging lens, the spatial filter including a first portion away from the optical axis and a second portion adjacent to the optical axis; and
an image capturing element for capturing the tomography image of the object through the imaging lens by adjusting a focus position of the object lens relative to the object,
wherein the first portion of the spatial filter transmits light which is incident on the object lens at a predetermined angle with respect to the optical axis so as to transmit light from the object, and the second portion of the spatial filter blocks light which is incident on the object at an angle smaller than the predetermined angle with respect to the optical axis so as to block light from the light scattering medium.

15. A method for obtaining a tomography image of an object in a light scattering medium using an optical system including an object lens and an imaging lens and an image capturing element, the method comprising the step of:
receiving light from the object through the object lens;
directing light which is incident on the object lens toward the imaging lens;
filtering the light from the object lens toward the imaging lens, said filtering step comprising: transmitting light which is incident on the object lens at a predetermined angle with respect to an optical axis of the object lens; and blocking light which is incident on the object lens at an angle smaller than the predetermined angle with respect to the optical axis;
projecting the filtered light on the image capturing element;
changing a focus position of the optical system; and
thereby generating a tomography image of the object.

16. The method according to claim 15, further comprising the step of illuminating the object.

17. An optical system for obtaining a tomography image of an object in a light scattering medium comprising:
an object lens;
an imaging lens disposed on an optical axis of the object lens;
a spatial filter disposed on the optical axis between the object lens and the image lens, the spatial filter including a first portion away from the optical axis and a second portion adjacent to the optical axis; and
an image capturing element for capturing the tomography image of the object through the imaging lens by adjusting a focus position of the object lens relative to the object,
wherein said first portion of the spatial filter transmits light which is incident on the object lens at a predetermined angle with respect to the optical axis so as to transmit light from the object, and the second portion of the spatial filter blocks light which is incident on the object lens at an angle smaller than the predetermined angle with respect to the optical axis so as to block light from the light scattering medium, and where the object lens and the imaging lens are arranged so that the rear focus of the object lens coincides with a front focus of the imaging lens.

18. An optical system for visualizing an object according to claim 17, wherein said spatial filter is disposed at the rear focus of the object lens.

19. An optical system for visualizing an object according to claim 17, wherein said object lens and said imaging lens have the same diameter and the same focal length with each other.

* * * * *